United States Patent [19]

Le Magnen et al.

[11] Patent Number: 5,397,577
[45] Date of Patent: Mar. 14, 1995

[54] METHOD FOR OBTAINING BETA CASEIN

[75] Inventors: Christine Le Magnen; Jean-Jacques Maugas, both of Rennes, France

[73] Assignee: Eurial - Parc Club du Perray, Nantes Cedex, France

[21] Appl. No.: 949,872

[22] PCT Filed: Jun. 25, 1991

[86] PCT No.: PCT/FR91/00506
  § 371 Date: Nov. 13, 1992
  § 102(e) Date: Nov. 13, 1992

[87] PCT Pub. No.: WO92/00017
  PCT Pub. Date: Jan. 9, 1992

[30] Foreign Application Priority Data

Jun. 25, 1990 [FR] France .................. 90 07951

[51] Int. Cl.$^6$ .................................................. A61K 35/20
[52] U.S. Cl. ..................................... 424/535; 429/491
[58] Field of Search ......................... 424/535; 426/491

[56] References Cited

FOREIGN PATENT DOCUMENTS 59-091849 5/1984 Japan .

Primary Examiner—Douglas W. Robinson
Assistant Examiner—Jean C. Witz
Attorney, Agent, or Firm—Omri M. Behr; Matthew J. McDonald

[57] ABSTRACT

A method for obtaining beta casein by separating it from para kappa casein involving the use of rennet casein is disclosed.

13 Claims, 3 Drawing Sheets

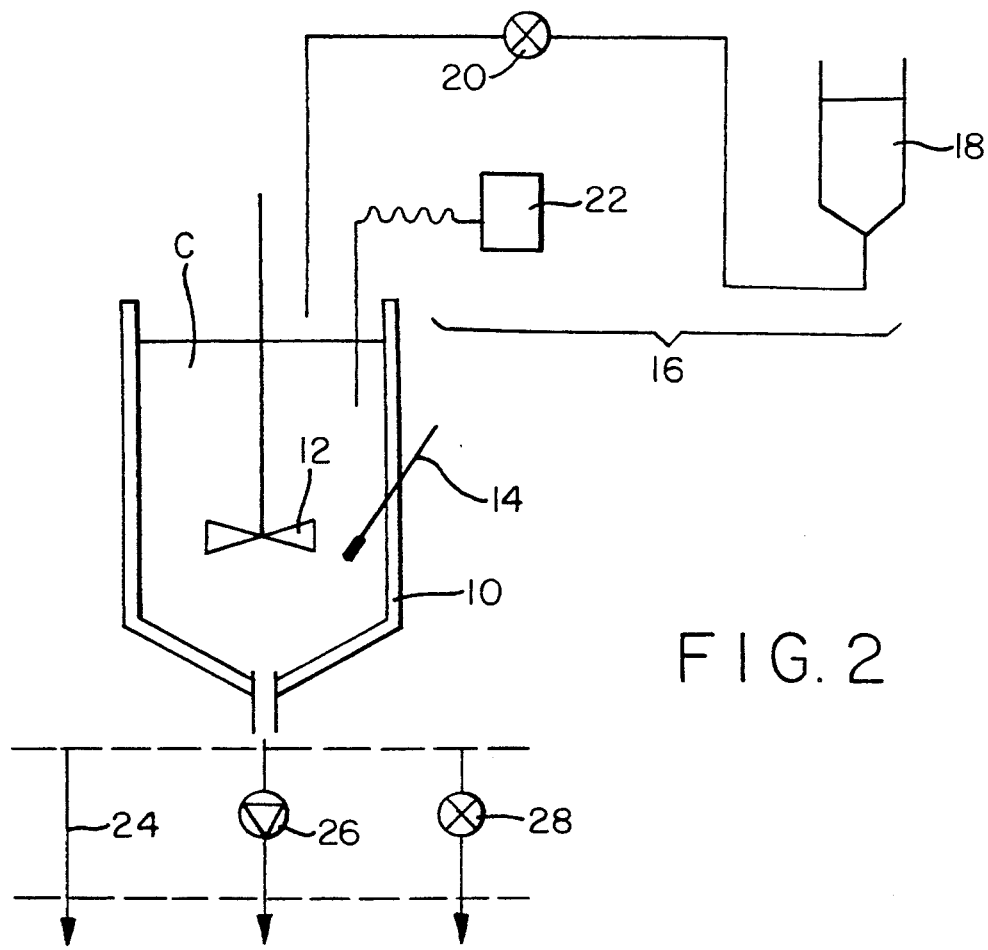
FIG. 2
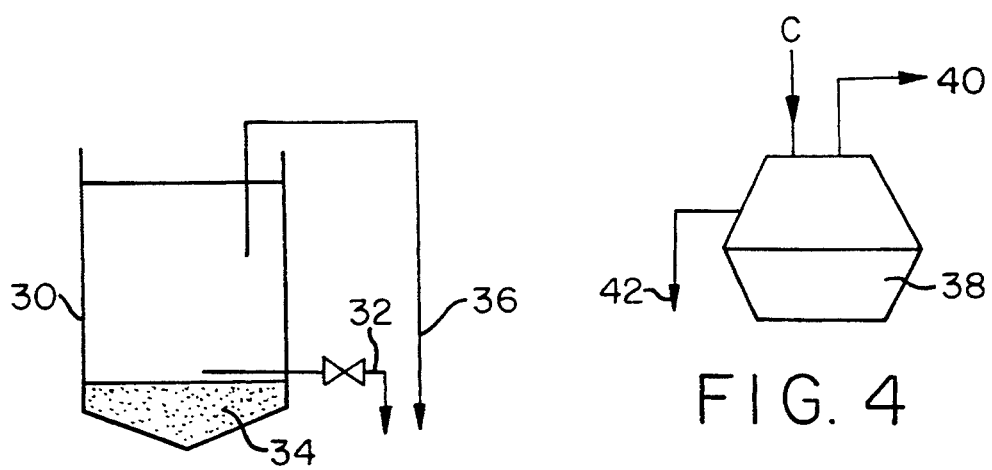
FIG. 3
FIG. 4
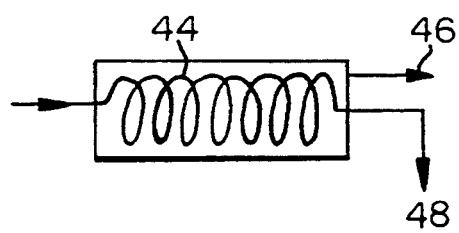
FIG. 5

METHOD FOR OBTAINING BETA CASEIN

The invention relates to the obtaining of beta casein from rennet casein. It relates more particularly to a method and also to a device adapted to obtain a solution of beta casein from a suspension or solution of rennet casein.

It is known to obtain rennet casein from the precipitation of micells of caseins of a mammal milk after hydrolysis of the casein by the rennet or by any other enzyme or mixture of enzymes of animal, vegetable, bacterial or fungal origin capable of hydrolyzing the pHe-Met 105-106 bond of kappa casein. After the separation of the lactoserum and the washing of the curds, an insoluble product is obtained which contains all the caseins of the milk thus used, except for the hydrophilic fraction which stabilizes the micell and is released by the enzyme—i.e., the caseino macropeptide. The other product of the enzymatic reaction is referred to as para kappa casein.

Amongst the caseins present in this insoluble product produced by the curdling of mammal milks, beta casein is known to have numerous functional, technological and physiological properties bound up with its physico-chemical characteristics. These properties include more particularly:

foaming and emulsifying properties conferred on beta casein by its strong hydrophobicity. This property also plays a part in the stabilization of the micellar structure in association with the colloidal phosphate and plays a part in the texture of cheese-making curds;

nutritional properties resulting from its amino acid composition, providing considerable richness in lysine and tryptophane;

properties enabling it to be used in the pharmaceutical industry, since the hydrolysis of beta casein leads to:

the obtaining of phosphopeptides which play a role in the intestinal absorption of mineral elements, and the formation of a hexapeptide known as beta casomorphine, which seems to play a role comparable to opiate derivatives which influence sleep, the secretion of insulin and control of the appetite.

It is known that beta casein has the property of becoming solubilized when the temperature goes down and the quantity of beta casein dissociating cold from the micell increases in the course of time, although 75% of this quantity is released in the first 15 minutes (CREAMER et al, NZ J. Dairy Science Technol. 12, 58-66, 1977).

The quantity of beta casein capable of cold solubilization also depends on the protein concentration used and also on the concentration of colloidal phosphate present (PIERRE and BRULE, Journal of Dairy Research 48, 417-428, 1981).

Having regard to the numerous properties of beta casein, it is clearly important to develop a process which can be economically used in industry and which enables beta casein to be separated from the other caseins present in the medium. In the past a certain number of attempts to solve this problem have been made.

One example of such an attempt is represented by French Patent No. 2 592 769, which discloses a method of obtaining a substance enriched in beta casein by separation of the beta casein from a mammal milk or a derivative of mammal milk, such as a caseinate, the process being more particularly performed by a molecular sieving technique using a micro-filtration membrane.

This prior art technique has a certain number of disadvantages, amongst which the following may be noted:

a difficulty in obtaining at one and the same time a high beta casein concentration and adequate purity, and extremely low cold micro-filtration performances, something which forms a certain handicap to the extrapolation of this process to the industrial level.

It is therefore an object of the invention to provide a new method for obtaining beta casein which is free from the disadvantages of the prior art methods and which can be used industrially. The invention starts from the realization that beta casein can be extracted from rennet casein and that such extraction gives excellent yields both in concentration and purity.

Accordingly a first aspect of the invention has for its object a process for obtaining a solution of beta casein from rennet casein as produced by the enzymatic curdling of milk. One of the original features of the process according to the invention in comparison with the prior art technique disclosed in French Patent No. 2 592 769 resides in the use not of a caseinate, but of a rennet casein in which kappa casein, the main contaminant found in the extraction of beta casein, is hydrolyzed to form para kappa casein, which has a much lower solubility.

The method according to the invention is therefore characterized in that the suspension or solution of rennet casein, for example, as formed by the enzymatic curdling of a mammal milk is cooled to a temperature of the order of approximately $-2°$ C. to $+10°$ C., preferably between $+2°$ C. and $+5°$ C. and its pH is adjusted to a value of approximately 4.00 to 5.00, and separating the suspension or solution of rennet casein thus cooled and acidified into two phases, so as to obtain a solid phase and a liquid phase, the latter containing the beta casein.

In the method according to the invention it is possible to use more particularly as the mammal milk, cows or goats milk, the rennet casein originating from the enzymatic curdling of said mammal milk by a mixture of enzymes known as rennet enzymes or by an enzyme of animal, vegetable, bacterial, fungal origin or by a mixture of these different enzymes enabling the casein to be hydrolyzed.

The rennet casein can be used in suspension in water or in a saline solution and can thus be partially or completely solubilized. The salts which can be used include more particularly sodium, potassium or ammonium chlorides, sodium, potassium or ammonium citrates, sodium, potassium or ammonium oxalates, sodium, potassium or ammonium phosphates, the salts being usable on their own or in various mixtures. Preferably the concentration of salts or of a mixture of different salts used in the solution can vary from approximately 0.1 to 4%.

Preferably according to the invention the concentration of rennet casein present in the suspension or solution can vary from 1 to 10%, preferably from approximately 4 to 7%.

In the first stage of the method according to the invention the pH of the cooled suspension or solution of rennet casein is adjusted to the aforementioned value of approximately 4.00 to 5.00 by the addition of an organic or mineral acid, or of a mixture of these two types of acids. The organic acid used can be more particularly acetic acid, citric acid, lactic acid, oxalic acid, either separately or in various mixtures. The mineral acid which can be used is more particularly hydrochloric acid, sulphuric acid, nitric acid, phosphoric acid, either separately or in various mixtures. Of course, the pH of the suspension or solution of rennet casein is so controlled as to be kept constant during the whole of this first phase of the method according to the invention.

According to the invention the step of acidification and control of the pH of the solution or suspension of rennet casein can be performed prior to the stage of adjusting the temperature to values required by the method and set forth hereinbefore.

Following this chemical step of the method, the suspension or solution of rennet casein which has thus been cooled and whose pH has been adjusted is present in the form of a mixture of two phases:

a liquid phase containing the beta casein and
a sedimentable phase containing the remainder of the unsolubilized caseins.

In the second step of the method according to the invention, the two phases are separated physically either by natural decantation, or using a suitable apparatus, as will be disclosed hereinafter in the description of an embodiment of the device for the performance of the method according to the invention.

After said separation the liquid phase enriched in beta casein is recovered by any suitable means, as will be disclosed hereinafter.

The method defined hereinbefore makes beta casein available which has a degree of purity higher than approximately 90% in relation to the total protein material, as measured by HPLC and electrophoresis. This product is advantageously free from chemical additives such as those used in the prior art separating techniques, such as denaturing agents, precipitating agents or urea. It is a novel product which enters as such into the scope of the invention.

This product is more particularly characterized in that it contains practically no kappa casein.

The beta casein as obtained by the method according to the invention is also characterized in that it has a pH close to neutrality. The properties of this product are advantageously used as a food or food complement in the foodstuffs and dietetic, cheese-making and dairy industries. In dietetics it forms a very advantageous raw material for obtaining peptides.

The beta casein according to the invention is also very advantageous in the pharmaceutical or cosmetics industry.

The invention also relates to the coproduct of the beta casein isolated according to the invention, represented by the solid phase formed during the cooling and acidification of the suspension or solution of rennet casein. This coproduct, which is substantially totally free from beta casein, has original functional, physiological and nutritional properties.

It therefore finds applications in the aforementioned industries. This coproduct can also be used as a raw material for the purification of the other contaminants of micells, such purification being facilitated by the fact that this coproduct contains practically no beta casein.

In a second aspect, the invention relates to a device for the performance of the method as defined hereinbefore, the device being characterized in that it comprises:

a reactor into which the solution or suspension of rennet casein produced by the enzymatic curdling of mammal milk is introduced;

cooling means enabling the temperature of the suspension in the reactor to be maintained at a value of approximately $-2°$ C. to $+10°$ C., preferably between $+2°$ C. and $5°$ C.;

a pH-stat enabling the quantity of acids added to the solution or suspension of rennet casein contained in the reactor to be regulated, under the control of a pH-meter, and means for ensuring the separation of the liquid and sedimentable phases contained in the mixture originating from said reactor.

Other features and advantages of the invention will be gathered from the following description, with reference to the accompanying drawings which illustrate various completely non-limiting embodiments thereof and wherein:

FIG. 2 shows diagrammatically the device for the performance of the method;

FIGS. 3 to 5 are diagrams illustrating the various embodiments of the means for separating the two phases coming from the first step of the method according to the invention.

Figure 1:
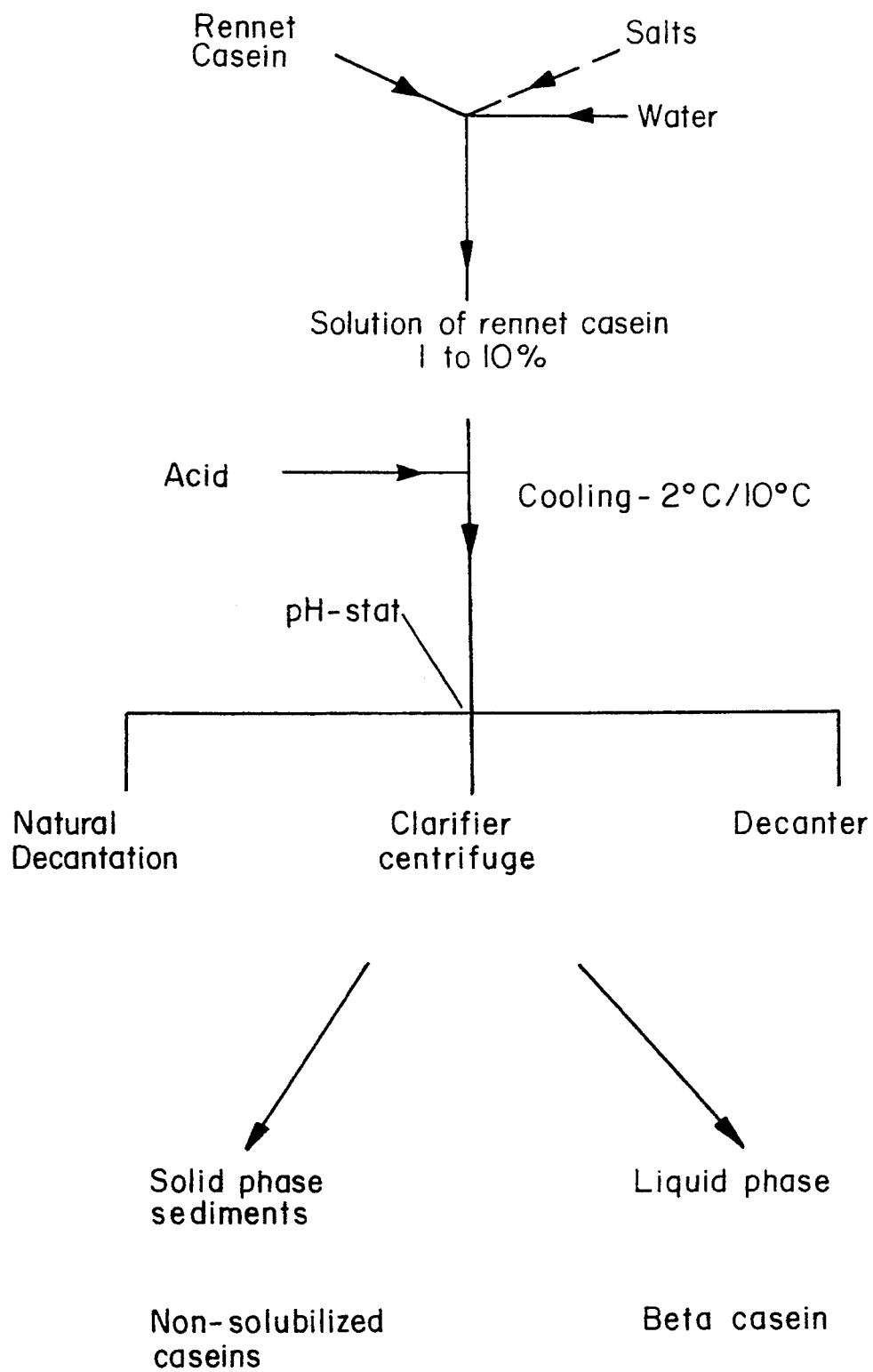
FIG. 1 is a diagram illustrating the steps of the method according to the invention for obtaining the solution of beta casein.

Referring to the drawings, the solution or suspension of rennet casein C is introduced into a jacketed receptacle or reactor 10, so as to maintain therein the temperature of said solution or suspension at the value specified by the method—i.e., between approximately $-2°$ C. and $+10°$ C., preferably between $+2°$ C. and $+5°$ C. A cooling solution circulates in the jacket of the reactor 10 and the solution or suspension of rennet casein C is subjected to slight agitation by means of a variable speed agitator 12. The temperature is controlled, for example, by a thermometer 14.

The pH of the cooled solution or suspension of beta casein C is maintained at the constant value specified by the method mentioned hereinbefore by means of a pH-stat 16, which allows the control of the quantity of acid delivered by a metering pump 20 from a feed 18 tank under the control of a pH-meter 22. The pH-stat 16 is given a required value and the metering pump 20 enables the pH of the solution or suspension C to be adjusted in accordance with said required value, by delivering to the reactor 10 the necessary quantity of acid (or mixture of acids).

As indicated hereinbefore in the description of the method according to the invention, the suspension or solution coming from the reactor 10 takes the form of a mixture of two phases: a liquid phase and a sedimentable phase, and the device comprises means enabling the two phases to be separated so as to enable the liquid phase containing the beta casein to be recovered.

According to the invention the mixture of the two phases coming from the reactor 10 can be vehicled either directly by gravity (arrow 24 in FIG. 2) or by means of a volumetric pump 26 or centrifugal pump 28, via a conduit which may be cooled or not.

The means used to separate the liquid phase containing the beta casein from the sedimentable phase can be formed, for example, by:

a clarifier of self-clearing or non-self-clearing type operating with an acceleration from approximately 500 to 8000 g, preferably from 1500 to 3000 g;

a decanter operating with an acceleration of approximately 500 to 8000 g, preferably 1500 to 3000 g, or a centrifuge operating with an acceleration of 500 to 8000 g.

These means can be cooled or not, in dependence on the varying dwell time of the products in the installation.

Outstanding results can also be obtained in the separation of the two phases by performing decantation at atmospheric pressure into the receptacle containing the mixture of the two phases.

FIG. 3 illustrates this embodiment. A receptacle 30 receives the mixture of the two phases coming from the reactor 10. In the receptacle the liquid phase, which represents the supernatant enriched with beta casein, is recovered either via an orifice 32, with which the wall of the receptacle 30 is formed for this purpose immediately above the precipitated phase (sediments 34), or by simple siphoning, possibly using a volumetric pump or a centrifugal pump (this possibility is illustrated by arrow 36 in FIG. 3).

The diagram in FIG. 4 shows a centrifuge or clarifier 38 enabling the two phases of the solution C coming from the reactor 10 to be separated. In this variant the liquid phase containing the beta casein is recovered, for example by siphoning (indicated diagrammatically by arrow 40), and the sediments are evacuated via a conduit 42.

Lastly, the diagram in FIG. 5 illustrates the variant using a decanter 44 for the separation of the two phases. The liquid phase containing the beta casein is recovered at place 46 and the sediment evacuated via a conduit 48.

The device according to the invention disclosed hereinbefore can operate either intermittently or continuously.

The following is a Table showing the results of test performances of the method according to the invention. The Table includes five embodiments of the invention for obtaining a solution of beta casein from rennet casein with different concentrations and using different continuously or intermittently operating devices. Of course, these examples merely illustrate the method according to the invention and are in no way limiting. The same thing applies to the device disclosed hereinbefore with reference to the accompanying drawings, of which variant embodiments may be envisaged without exceeding the scope of the invention.

TABLE

Figure 6:
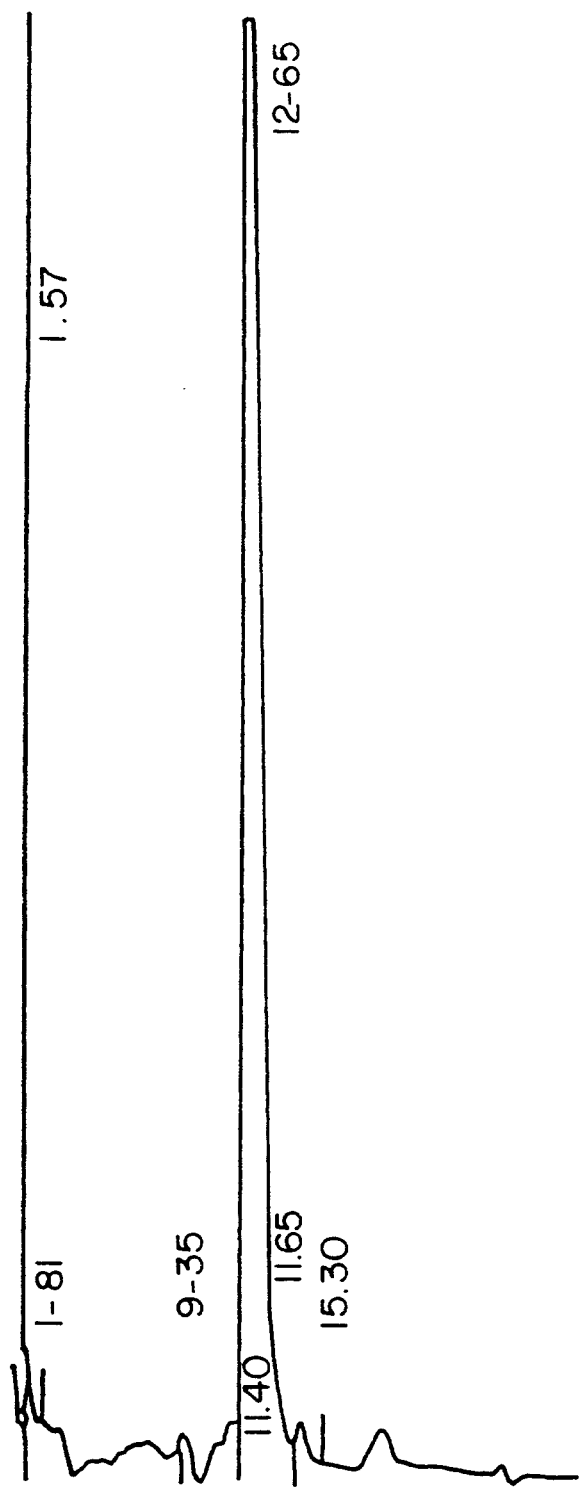
FIG. 6 shows the chromatographic profile of a sample (HPLC).

| Raw material | Separator type | Flow rate m3/h | Force g | Supernatant % | C g/l | C purity |
|---|---|---|---|---|---|---|
| 1 Rennet casein | C.n.c. | | 2500 | 93 | 1.3 | >99 |
| 2 Rennet casein | D c | 1 | | 90 | 3.5 | 95 |
| 3 Rennet casein | C.n.c. | | 2500 | 90 | 3.8 | 95 |
| 4 Rennet casein | C.n.c. | | 2500 | 86 | 5.3 | 95 |
| 5 Rennet casein | DG c | 1 | | 86 | 5.0 | >98 | n.c = intermittent operation
c = continuous operation
C = decanter
DG = Guinard decanter FIG. 6 shows a chromatographic profile (HPLC reverse phase analysis) of a sample corresponding to the following analysis:

| Total solids | 995 g/kg |
| Nitrogen | 945 g/kg beta casein > 900 g/kg |
| Mineral substances | 50 g/kg |
| Calcium | 5 g/kg |
| Sodium | 16 g/kg |
| Potassium | 0.1 g/kg |
| Phosphoruses | 11.1 g/kg |

The values indicated in FIG. 6 corresponds to the elution time. The obtaining of a peak at 12.65 proves that the product obtained has a purity greater than 90%.

We claim:

1. A method for obtaining beta casein comprising the steps: of
    a) enzymatically curdling mammalian milk, to form a suspension or solution of rennet casein comprising para kappa casein and beta casein,
    b) cooling the thus produced suspension or solution of rennet casein,
    c) adjusting the pH to acid values, whereby said cooling and pH adjustment of said solution or suspension of rennet casein causes the formation of a solid and a liquid phase,
    d) separating said solid phase from said liquid phase, the former containing the para kappa casein and the latter containing the beta casein.

2. The method according to claim 1 wherein the enzyme used is selected from the group consisting of a mixture of enzymes of rennet type, an enzyme of animal, vegetable, bacterial or fungal origin, or a mixture of said different enzymes.

3. The method according to claim 1, wherein the cooling step is carried out at a temperature of +2° C. to +5° C.

4. The method according to claim 1 wherein the concentration of the rennet casein present in the suspension or solution of rennet casein thus produced is of the order of 1 to 10%.

5. The method according to claim 1 wherein the rennet casein is diluted in water or in a saline solution formed by water and 0.1 to 4% of salts selected from sodium, potassium or ammonium chlorides, sodium, potassium or ammonium citrates, sodium, potassium or ammonium oxalates, sodium, potassium or ammonium phosphates or mixtures thereof prior to cooling or pH adjustment.

6. The method according to claim 1 wherein the pH of the cooled solution is adjusted by the addition of an organic acid or a mineral acid or a mixture of said two types of acid.

7. The method according to claim 6, wherein the organic acid used is acetic acid, citric acid, lactic acid, oxalic acid, or mixtures thereof, the mineral acid used being hydrochloric acid, sulfuric acid, phosphoric acid, nitric acid, or mixtures thereof.

8. The method according to claim 1 wherein the step of acidification of the solution or suspension of rennet casein is performed prior to the stage of controlling the temperature of said solution or suspension to values ranging from −2° C. to +10° C.

9. The method according to claim 4, wherein the concentration of rennet casein is of 4 to 7%.

10. The method according to claim 1, wherein said separation is performed by decantation at atmospheric pressure.

11. The method according to claim 1, wherein said separation is performed by clarification decantation.

12. The method according to claim 1, wherein said separation is performed by centrifugation.

13. A method for obtaining beta casein comprising the steps of a) enzymatically-curdling mammalian milk, to form a suspension or solution of rennet casein comprising para kappa casein and beta casein,
b) cooling the thus produced suspension or solution of rennet casein to a temperature of between $-2°$ C. and $+10°$ C.,
c) adjusting the pH to a value of 4.00 to 5.00,
d) separating the thus cooled and acidified suspension or solution of rennet casein into a solid phase and a liquid phase, the former containing the para kappa casein, the latter containing the beta casein.

* * * * *